US00PP18922P2

(12) United States Plant Patent
Heims

(10) Patent No.: US PP18,922 P2
(45) Date of Patent: Jun. 10, 2008

(54) ***HEUCHERA* PLANT NAMED 'CAFÉ OLÉ'**

(50) Latin Name: *Heuchera spp.*
Varietal Denomination: Café Olé

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 27 days.

(21) Appl. No.: 11/639,125

(22) Filed: Dec. 13, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Annette H Para
(74) *Attorney, Agent, or Firm*—Klarquist Sparkman, LLP

(57) ABSTRACT

A new and distinct *Heuchera* plant characterized by small jagged and ruffled leaves, dark foliage with purple backs, and a low, mounding habit.

1 Drawing Sheet

Botanical denomination: *Heuchera* spp.
Variety designation: 'Café Olé'.
Parentage: Unknown.

The present invention relates to a new and distinct cultivar of *Heuchera* hybrid and given the cultivar name of 'Café Olé'. *Heuchera* is in the family Saxifragaceae. *Heuchera* 'Café Olé' originated as a seedling from an open pollinated cross from unknown parents in a select group of unnamed, experimental, proprietary plants. It was selected for its attractive foliage and low mounding habit. Since the new variety has dark ruffled leaves it is probable that *Heuchera micrantha* and *Heuchera americana* are in its parentage.

This new *Heuchera* is distinguished by:

1. Small jagged and ruffled leaves.
2. Dark foliage with purple backs.
3. Low, mounding habit.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
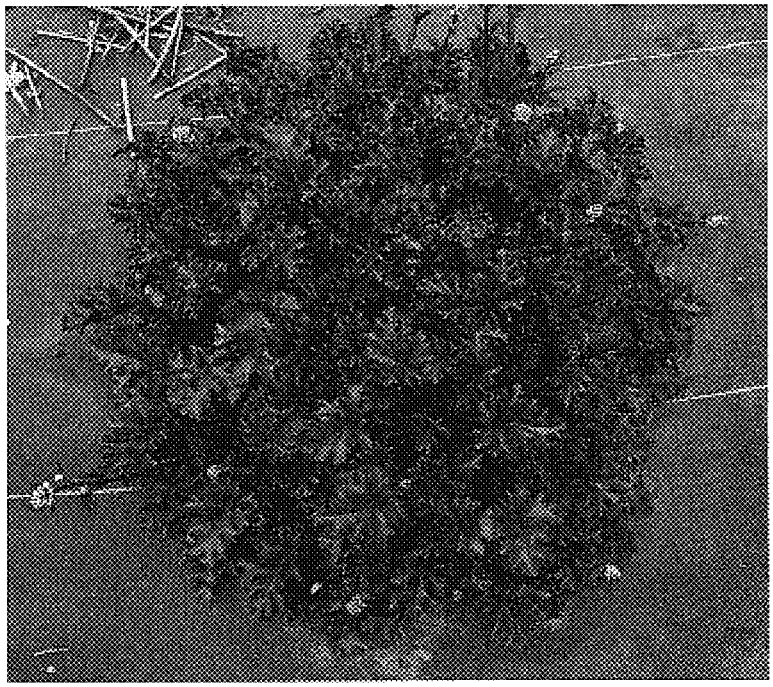
FIG. 1 shows a two-year-old plant of *Heuchera* 'Café Olé' growing in the ground in the trial fields in April in Canby, Oreg.
Figure 2:
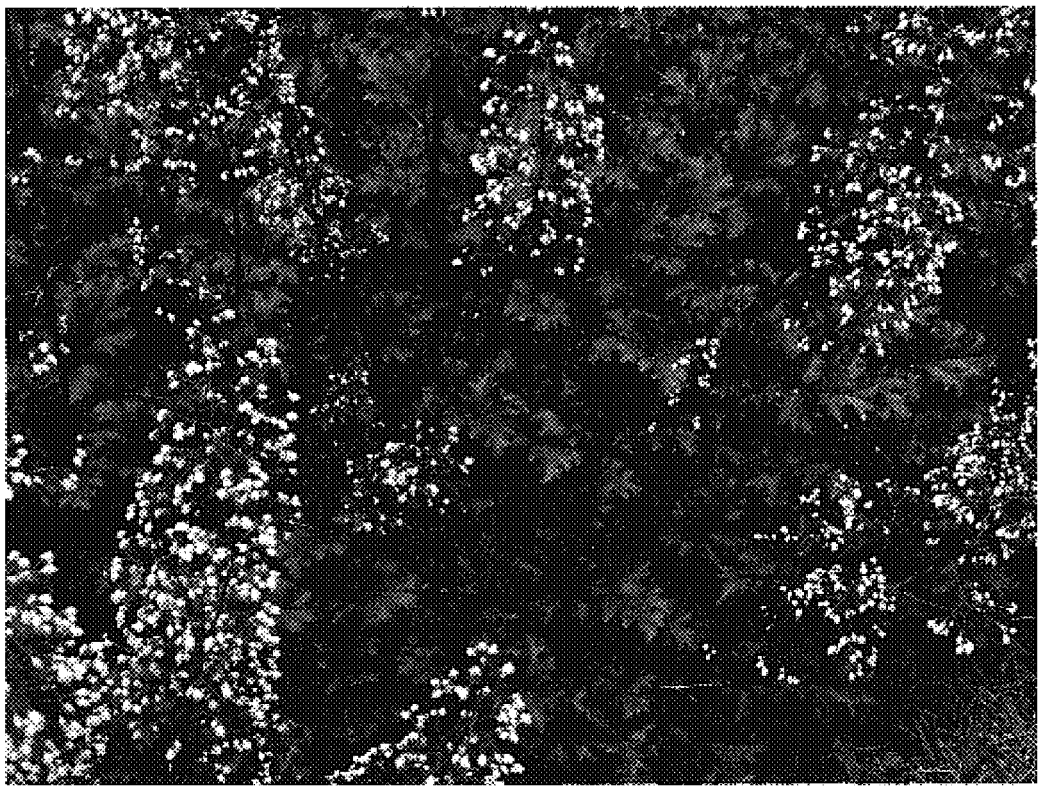
FIG. 2 shows a mass of two year old plants in flower in mid June growing in the ground in the garden in Canby, Oreg.

The following is a detailed description of the new *Heuchera* cultivar based on observations taken in June of a three-year-old specimen in the ground in full sun under typical outdoor conditions in the trial fields in Canby, Oreg. Canby is in Zone 8 on the USDA Hardiness map. Temperatures range from a high of 95 degrees F. in August to 32 degrees F. in January. Normal rainfall in Canby is 42.8 inches per year. The color descriptions are all based on The Royal Horticultural Society Colour Chart.

Plant:
- *Form.*—Basal rosette, herbaceous perennial.
- *Hardiness.*—USDA Zone 4 to 9.
- *Size.*—15 cm tall from the ground to the top of the leaves and 40 cm wide.
- *Habit.*—Mounding.
- *Vigor.*—Excellent.
- *Roots.*—Fibrous, freely branching, fine, and white in color; roots develop slowly from cuttings.

Leaf:
- *Type.*—Simple.
- *Arrangement.*—Rosette.
- *Shape.*—Ovate.
- *Lobing/division.*—5 to 7 main lobes, with 1 to 2 shallow secondary lobes.
- *Venation.*—Palmate.
- *Margins.*—Coarsely crenate and undulate.
- *Apex.*—Mucronulate.
- *Base.*—Cordate, lobes overlapping at the base.
- *Blade size.*—Grows to 6 cm long and 5 cm wide.
- *Surface texture.*—Glabrous, margins glandular.
- *Petiole.*—Grows to 9 cm long and 2 mm wide, with glandular hairs, Greyed Purple 183A on young leaves to Greyed Orange 165A on mature leaves.
- *Leaf color.*—Spring and new leaves topside — Brown 200A summer, winter topside — Olive green, Between Yellow Green 147A and Brown 200A bottom side — Red Purple 59A.

Inflorescence:
- *Type.*—Thyrse.
- *Number of flowers.*—100 per thyrse.
- *Number of thyrse.*—12 in first spring flush.
- *Peduncle.*—With 0 to 5 cauline leaves, ovate, jagged, grows to 2.5 cm long and 2 cm wide, 50 cm tall and 4 mm wide near the base, glandular pubescent, Greyed Purple 187A.

*Pedicel.*—Variable in length, glandular pubescent, Greyed Purple 187A.

*Bloom period.*—April to May in Canby, Oreg.

Flower bud:

*Size.*—3 mm wide and 4 mm long.

*Description.*—Glandular, ovoid.

*Color.*—Yellow White 158B and Greyed Purple 184C.

Flower:

*Type.*—Perfect, zygomorphic.

*Shape.*—Campanulate.

*Size.*—4 mm long and 2 mm wide.

*Corolla.*—5 petals, White 155A, 2 mm long and 0.4 mm wide, spatulate with a clawed base, curling, margin entire, apex acute.

*Calyx.*—4 mm long and 2 mm wide, 5 lobes, divided ⅓ way to the base, glandular on the outside surface, glabrous inside, margin entire, apex acute.

*Calyx and overall flower color.*—Creamy white, Yellow White 158A on both inner and outer surfaces.

*Stamen.*—5 in number, sterile, filaments 3 mm long, Yellow White 158A overall.

*Pistil color.*—White 155A overall, 4 mm long.

*Fragrance.*—None.

*Lastingness.*—Each thyrse blooms for about 2 weeks on the plant.

Fruit:

*Type.*—Two-beaked ovoid capsule.

*Color.*—Grey Brown 199A.

Seed:

*Shape.*—Linear.

*Size.*—1 mm long.

*Color.*—Black 202A.

Pest and disease tolerance: Excellent disease resistance to powdery mildew, the common problem of *Heuchera.* Susceptible to root weevils. *Heuchera* rust does not seem to be a problem.

COMPARISON TO SIMILAR *HEUCHERA*

Compared to *Heuchera* 'Chocolate Ruffles' (U.S. Plant Pat. No. 8,965), *Heuchera* 'Café Olé' has a much smaller habit and leaves.

I claim:

1. A new and distinct hybrid of *Heuchera* plant as herein illustrated and described.

* * * * *